United States Patent [19]
Engelberg-Kulka et al.

[11] Patent Number: 5,830,673
[45] Date of Patent: Nov. 3, 1998

[54] BIOASSAY OF SELENIUM

[75] Inventors: Hanna Engelberg-Kulka, Jerusalem; Myriam Reches, Mevasseret Zion, both of Israel

[73] Assignee: Yissum Research Development Company Ltd. of Hebrew Univ. of Jerusalem, Jerusalem, Israel

[21] Appl. No.: 756,342

[22] Filed: Nov. 26, 1996

Related U.S. Application Data

[63] Continuation-in-part of Ser. No. 600,992, May 20, 1996, abandoned.

[51] Int. Cl.⁶ .............................. G01N 33/53; C12Q 1/26; C12N 15/70; C12N 9/04
[52] U.S. Cl. .................... 435/7.9; 435/320.1; 435/26; 435/190; 435/207; 435/252.3; 435/252.33; 536/23.2; 536/23.4
[58] Field of Search ....................................... 435/207, 190, 435/26, 18, 7.9, 320.1, 252.3, 252.33; 536/23.4, 23.2

[56] References Cited

U.S. PATENT DOCUMENTS 5,149,656  9/1992  Bitton et al. ............................. 435/288
5,272,078  12/1993  Larsen et al. ............................ 435/189

OTHER PUBLICATIONS

Zinoni et al. *PNAS*, vol. 87, pp. 4660–4664, Jun. 1990.
Gray et al. *PNAS*, vol. 79, pp. 6598–6602, Nov. 1982.
Heider et al. *EMBO*, vol. 11, No. 10, pp. 3759–3766, 1992.
Kopelowitz et al., *J. Mol. Biol.*, vol. 225, pp. 261–269, 1992.

*Primary Examiner*—Keith D. Hendricks
*Attorney, Agent, or Firm*—Kohn & Associates

[57] ABSTRACT

The invention relates to a plasmid carrying a selenium-specifying DNA sequence of the *E. coli* fdhF gene upstream of the *E. coli* lac'Z gene which permits the incorporation of selenocystein into β-galactosidase. Particular plasmids according to the invention are pRM2, deposited at the ATCC under No. 75594 and pRM4, deposited at the ATCC under No. 75595. The invention also relates to microorganisms transformed with a plasmid according to the invention having selenium dependent β-galactosidase activity. The invention provides a method for the quantitative determine of selenium in selenium derivatives in a biological sample comprising incubating microorganisms according to the invention in a suitable medium also containing said sample and measuring the level of β-galactosidase activity. The biological sample may be, e.g. a blood sample or a food sample.

29 Claims, 7 Drawing Sheets

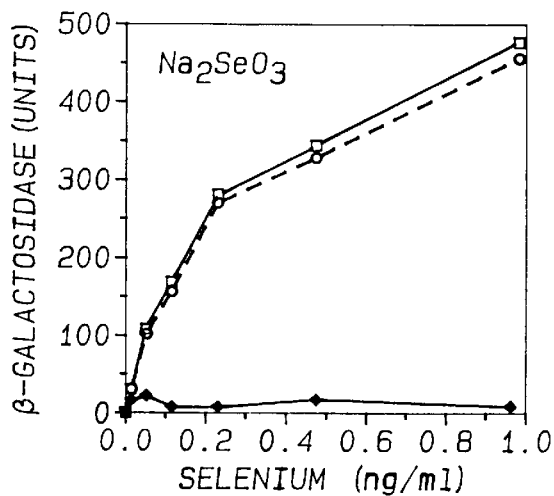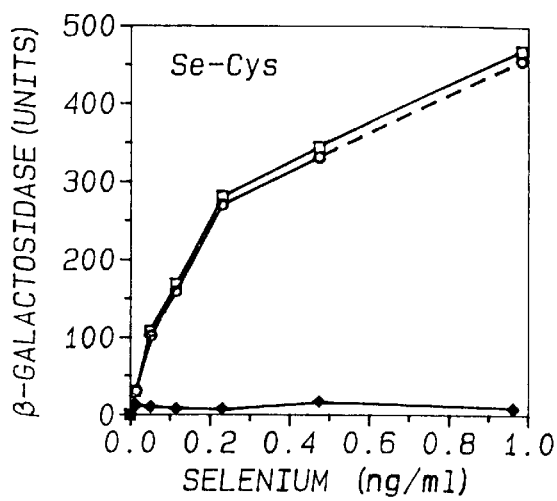
Fig-4A  Fig-4B
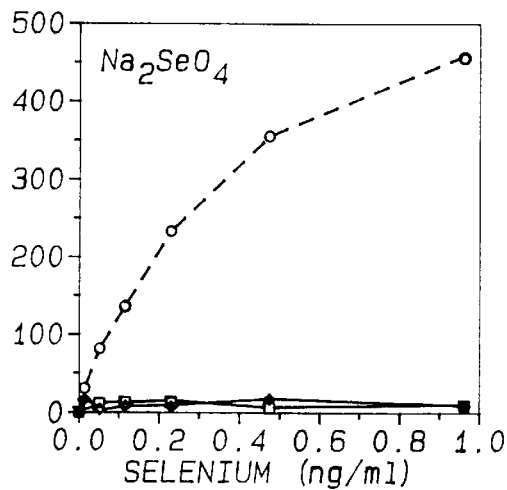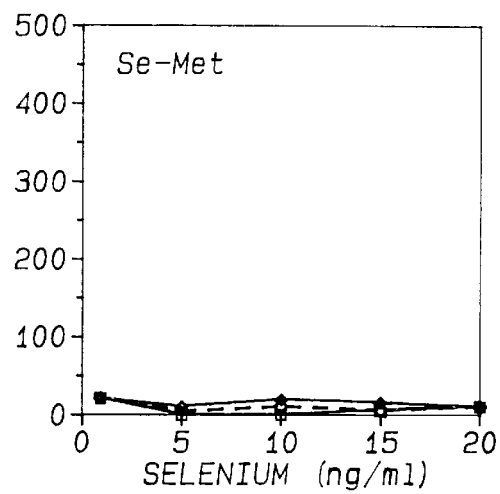
Fig-4C  Fig-4D
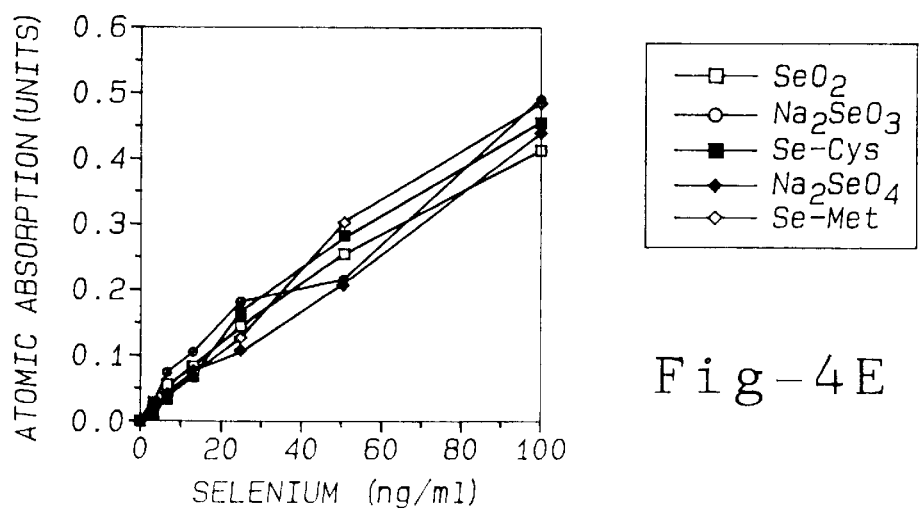
Fig-4E

BIOASSAY OF SELENIUM

This applications is a continuation-in-part of U.S. Ser. No. 08/600,992, filed May 20, 1996, now abandoned.

TECHNICAL FIELD

The invention relates to a bio-assay of selenium in selenium derivatives, transformed micro-organisms therefor, and plasmids suitable for generating said transformed micro-organisms.

BACKGROUND OF THE INVENTION

The trace element selenium is an essential component of several enzymes from various prokaryotic and eukaryotic organisms [for review see Stadtman, T. C. (199) J. Biol. Chem. 266, 16257–16260]. These enzymes have been shown to contain selenium in the form of a single selenocysteine residue in the active site of the enzyme [for review see Stadtman. T. C. (1990) Ann. Rev. Biochem. 59, 111–127; Sunde, R. A. (1990) Ann. Rev. Nutr. 10, 451–474)]. Among the seleno-containing proteins, the best known is the peroxide-destroying enzyme glutathione peroxidase (GPX) [Rotruck, J. T. et al. (1973) Science 179, 588–590; Epp, O. et al. Eur. J. Biochem. 133, 51–69]. Selenium, through its involvement with GPX, is one factor in a complex protective antioxidation mechanism that prevents intracellular damage by oxygen derived free radicals [for review see Halliwell, b. & Gutteridge, J. M. C. (1989) Free Radicals in Biology and Medicine (Claderon Press, Oxford) 2nd Edition]. Therefore, researchers in the field of human medicine and nutrition are studying the relationship of selenium in the diet and blood to free radical diseases like cancer [See, Beck et al., (1994) J. Med. Virol 43:166–170; Beck et al., (1995) Nature Med. 1:433–436; Berry et al., (1991) Nature 353:273–276; Neve (1991) Experimentia 47:187–193; Read (1990) New Scientist 125:38–42; Spinney, (1995) New Scientist 146:16; Taylor et al., (1994) J. Med. Chemistry 37:2637–2654].

Furthermore, as recently discovered, selenium is also involved in the form of selenocysteine in two additional human selenium-containing proteins. The first is the thyroid enzyme type 1 iodothyronine 5' dicodinase (5' diodinase) [Berry, et al, Nature 349:438–440] that converts thyroxine to the active thyroid hormone. The second is the plasma protein selenoprotein P [Read, et al, (199) J. Biol. Chem. 265:17899–17905; Hill, et al., J. Biol. Chem. 266:10050–10053] which actually contains 10 selenocysteine residues per subunit. Thus, selenium seems to have biochemical functions in addition to those associated with antioxidation, and may have a more general role in the maintenance of human health.

So far, low levels of selenium intake have clearly been shown to be associated with only two diseases, Keshan Disease [Yant et al., (1984) in Advances in Nutritional Research, ed. Draper, H. H. (Plenum Press, New York) pp. 203–231] and Kaschin Beck disease {Mo,D-X. (1987) in Selenium in Biology and Medicine, eds. Combs, G. F. et al., (Avi, Van Nostrand Heinhold, New York) pp. 924–233], both occurring in China. However, there are claims for the relationship between pronounced or even marginal selenium deficiencies and other diseases as well [Neve, J. (1991) Experientia 47, 187–193].

In recent years, there has been great interest in the field of selenium biochemistry and genetics. In-frame TGA codons have been found within the coding sequences of each of the genes encoding selenoproteins including the E. coli enzyme formate dehydrogenase (FDH) [Zinoni, et al., (1986) Proc. Natl. Acad. Sci. USA 83, 4650–4654; Zinoni, et al., Proc. Natl. Acad. Sci. USA 84, 3156–3160], mammalian proteins GPX [Chambers, et al (1986) EMBO J. 5, 1221–1227; Mullenbach et al, (1988) Protein Engineering 2, 239–246], 5' deiodinase [Berry et al (1991) ibid.; Berry, et al, (1991) Nature 353:273–276], and selenoprotein P [Read et al., (199) ibid.; Hill et al., (1991) ibid.]. It is now known that selenocysteine is coded by a UGA codon that usually acts as a termination codon. As has been shown in E. coli., several specific genes are involved in this incorporation process [for review see Bock, A. et al, (1991) TIBS. 16:463–467]. Of particular importance are the Gene selB, which codes for SelB protein, and selC, which codes for tRNA$^{Sec}$ [Lee, et al. (1990) Mol. Cell. Biol. 10:1940–1949]. This tRNA is charged with selenocysteine and is thus responsible for selenocysteine incorporation into polypeptides. In addition, a selenium-specific 47 nucleotide long codon context of the UGA codon in the E. coli. FDH gene (fdhF) has been identified [Zinoni, et al. (1990) Proc. Natl. Acad. Sci. USA 87, 4660–4664] that permits the UGA codon to be read as a selenoscysteine codon rather than as a termination codon. This context can form a stem-loop structure (as may be seen in FIG. 1E herein). Because of the presumed interaction of this stem-loop structure with SelB protein, the codon context seems to be required for selenocysteine incorporation [Heider et al, (1992) EMBO J. 11:3759–3766].

The assays currently available for determining selenium concentrations in various compounds are mainly physical or chemical methods by which the element selenium is determined directly [Ihnat, et al., (1986) Acta Pharmacol Toxicol. 59, 566–572; Neve, (1991) J. Trace Elem Electrolytes Health Dis. 5:1–17]. However, the known prior art methods for quantitative determination of selenium require sophisticated and expensive equipment, are not very specific and are also not sensitive to very low concentrations of selenium.

The present invention offers a simple, relatively inexpensive bio-assay that relates linearly and specifically to very low concentrations of selenium in several simple selenium derivatives. The bio-assay of the invention is carried out in E. coli and employs specific novel recombinant DNA plasmid constructs built for this specific purpose and measures only selenium compounds which are included in pathways of "real" selenoproteins. The bio-assay of the invention is suitable for the determination of the selenium in blood and also other biological materials and has several advantages over procedures currently used for this purpose.

BRIEF DESCRIPTION OF THE INVENTION

The invention relates to plasmids carrying a selenium specifying DNA sequence of the E. coli fdhF gene upstream of the E. coli lac'Z gene which permits the incorporation of selenocysteine into β-galactosidase.

More particularly, the plasmids according to the invention comprise at their beginning a lac'Z derivative carrying at least the −9 to +47 nucleotide bases of the TGA codon region of E. coli fdhF gene.

Preferred plasmids according to the invention comprise at their beginning a lac'Z derivative consisting of nucleotide bases −9 to +47 or −1 to +47 of the TGA codon region of E. coli fdhF gene.

Especially preferred are plasmids pRM2 deposited at the ATCC under No. 75594 and pRM4 deposited at the American Type Culture Collection (ATCC) Rockville, Md. U.S. under No. 75595.

In a further aspect, the invention relates to microorganisms transformed with a plasmid according to the invention having selenium-dependent β-galactosidase activity, *E. coli* being preferred.

Furthermore, the invention provides a method for quantitative determination of selenium in selenium derivatives in a biological sample comprising incubating transformed microorganisms according to the invention in a suitable medium also containing said sample and measuring the level of β-galactosidase activity.

The method of the invention may further comprise a preliminary step in which said biological sample is subjected to treatment with acid vapor prior to being added incubation medium.

The method according to the invention is particularly suitable for the determination of selenium in biologically active selenium derivatives and can be employed for the determination of selenium derivative in blood samples, food samples and in other biological materials.

Additionally, the invention relates to a diagnostic kit for the quantitative determination of selenium in selenium derivatives in accordance with the method of the invention.

DESCRIPTION OF THE FIGURES

Other advantages of the present invention will be readily appreciated as the same becomes better understood by reference to the following detailed description when considered in connection with the accompanying drawings wherein:

FIG. 4 The effect HCl-vapor treatment on simple Se derivatives used for the bio-assay. The assay described in FIG. 3 was used to determine levels of selenite (A), selenocysteine (B), selenate (C), and selenomethionine (D) which were applied either directly to *E. coli* YN3230 carrying the SelC gene (--□--), or after HCl-vapor treatment to either strain YN3230 (--■--) or to its SelC derivative (--◇--). The selC *E. coli* derivative RM2 was used as a control. The Se-containing compounds (selenite, selenocystein, selenate, and selenomethionine) were used either directly or after HCl-vapor-hydrolysis treatment. Only compounds treated with HCl vapor were used with the SelC derivative RM2 control strain. (E) Determination of Se concentration in several Se-containing compounds by AAS. carried out as in FIG. 3.

DETAILED DESCRIPTION OF THE INVENTION

The present invention relates to a specific and sensitive bioassay for the quantitative determination of selenium in selenium derivatives in biological materials, to transformed micro-organisms to be used therewith and to plasmids for generating these transformed microorganisms.

Recombinant DNA technology has been used to provide reporter systems than can be used generally to detect cis-acting elements such as regulatory sites or trans-acting elements such as proteins, RNA, and other large biological molecules. This approach has now been used in a new way to measure the presence and concentration of the essential chemical trace element selenium.

The present invention is based on the finding that (i) selenium is incorporated into polypeptides in the form of selenocysteine; and (ii) in $E.$ $coli$, this incorporation is permitted by the presence of a TGA codon within a specific codon contest [Zinoni et al. (1990) ibid.; Heider et al. (1992) ibid.]. Such a selenium-specific TGA codon context is present in the $E.$ $coli$ fdhF gene which specifies for the selenium-containing enzyme formate dehydrogenase [Zinoni et al.(1990) ibid.] These selenium-specifying sequences of the fdhF gene were inserted upstream from the $E.$ $coli$ lac'Z gene at the junction of the artificially fused genes λCI'-lac'I"Z located on plasmids pRM2 and pRM4 (Table 1B).

Figure 1:
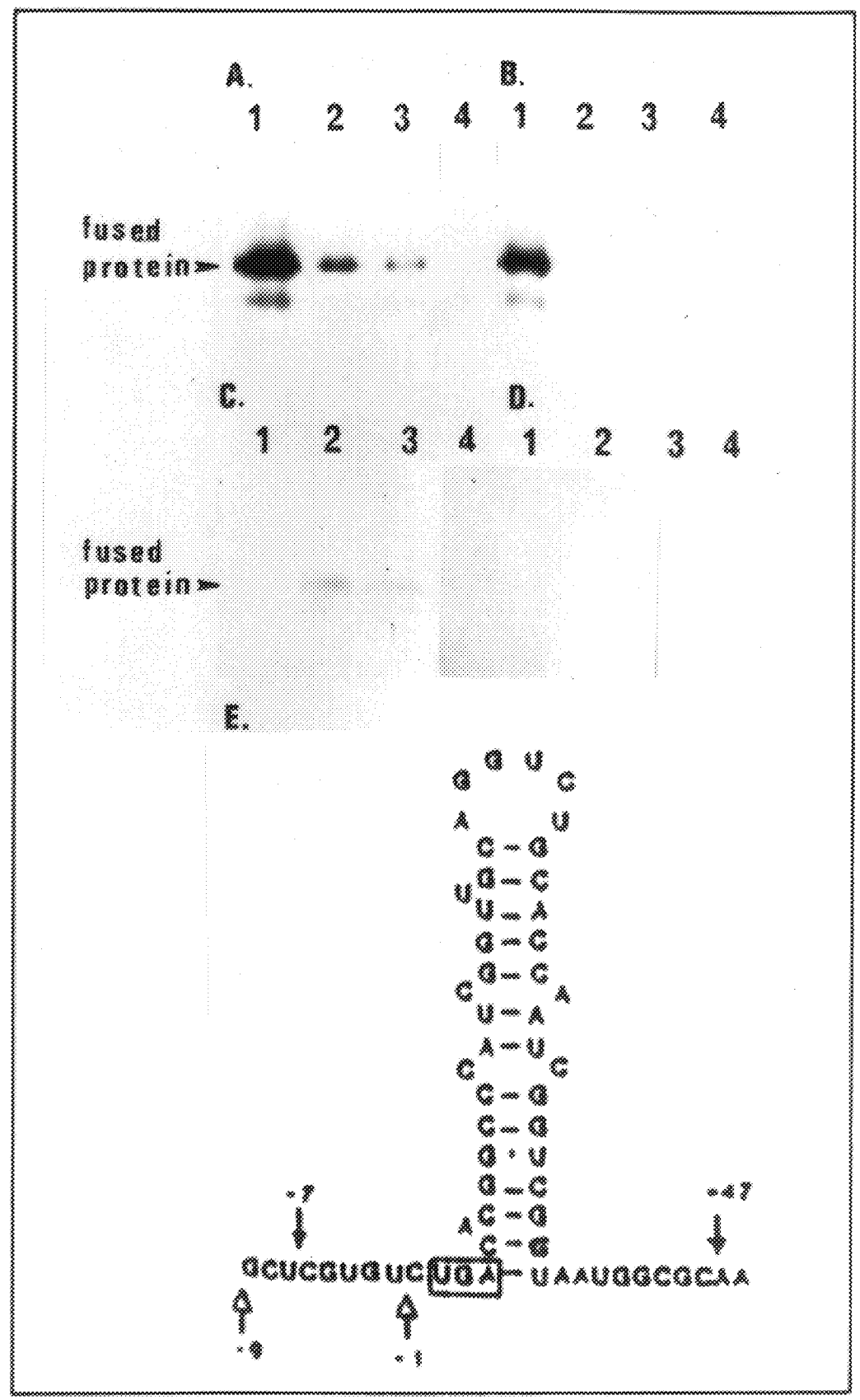
FIG. 1 The synthesis of a selenium-dependent fused protein directed to plasmids pRM2 and pRM4 *E. coli* strains MC4100 (A and C) and its selC derivative RM1 (B and D) were transformed by plasmids pMR1 (slot 1), pRM2 (slot 2), pRM4 (slot 3), and pMR1 (TGA$\underline{C}$) (slot 4). Freshly transformed cells were grown in M9 minimal medium, labeled either with [$^{35}$S]-methionine (A and B) or with [$^{75}$Se]-selenite (C and D). The labeled cells were lysed and subjected to electrophoresis on 7.5% SDS-polyacrylamide gels which were subsequently autoradiographed. Prior to electrophoresis, the [$^{35}$S]-methionine labeled lysates were treated with antibodies against β-galactosidase and immunoprecipitated. For details, see Materials and Methods. The position of the 140kD fused protein product of genes λcI-lacI"Z is indicated in the gel by an arrow. (E) The TGA containing segment of the *E. coli* fdhF gene present in plasmid pRM2 (nucleotides −1 to +47) and pRM4 (nucleotides −9 to +47). Here the segment is shown as an RNA molecule in its secondary structure according to Zinoni et al. [(1990) ibid.]. The UGA codon is boxed.
Figure 2A:
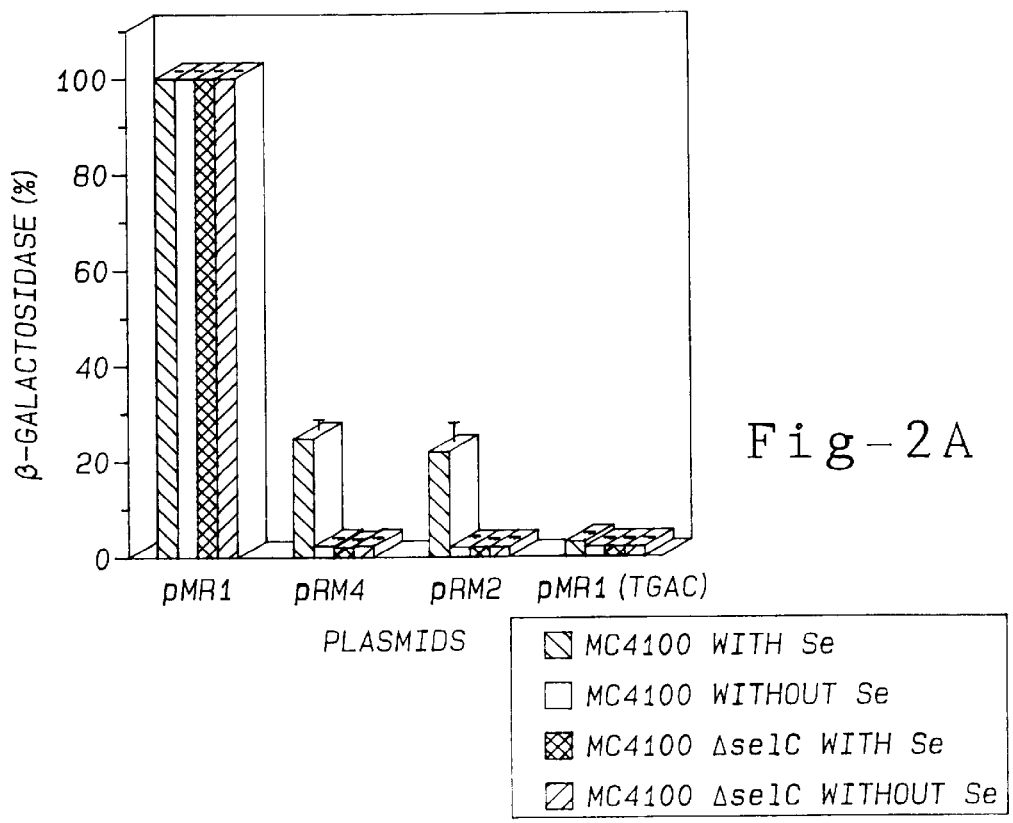
FIG. 2 The selenium-dependent synthesis of β-galactosidase directed by plasmids pRM2 and pRM4 in *E. coli*. *E. coli* strain MC4100 and its selC derivative RM1 (A) and strain YN3230 and its selC derivative RM2 (B) were transformed by each of the plasmids pMR1, pRM2, pRM4 and pRM1 (TGA$\underline{C}$). Freshly transformed cells were grown in M9 medium to mid-log phase in the absence or presence of sodium selenite (final concentration 1 μM/ml). Levels of β-galactosidase activity were determined as described previously [Kopelowitz (1992) ibid., for details see Materials and Methods]. The results represent at least three independent experiments. The figures for percent of β-galactosidase activity have been normalized taking the activity directed by plasmid pMR1 as 100%.
Figure 2B:
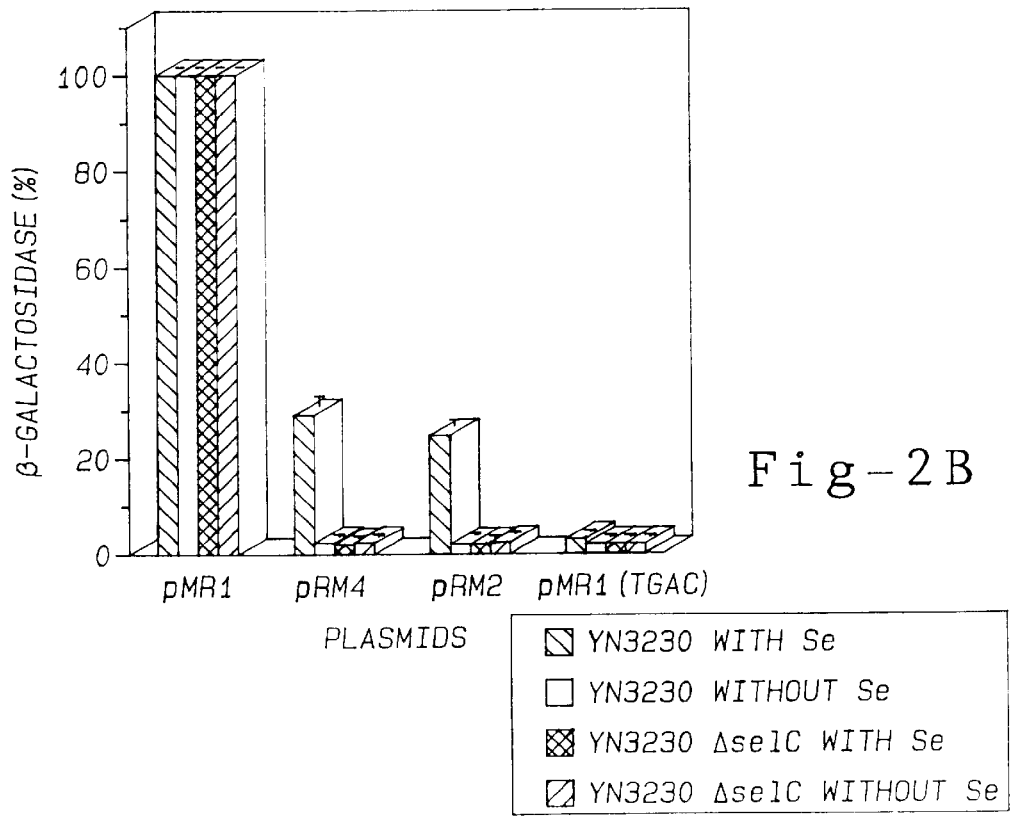
Figure 3A:
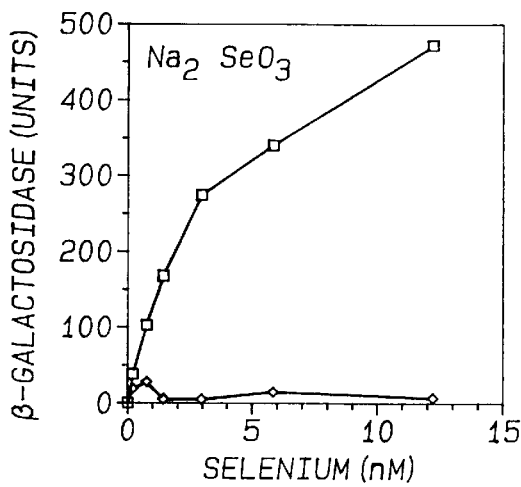
FIG. 3 Determining the concentrations of several simple selenium-containing compounds: the bio-assay (A–D) versus Atomic Absorption Spectrophotmetry (E). *E. coli* strain YN3230 (-□-) and its selC derivative RM2 (- -) were transformed by pRM4. The transformed cells were grown to mid-log phase in M9 medium in the presence of various concentrations of selenite 3 (A), selenocysteine (B), selenate (C), and selenomethionine (D). The levels of β-galactosidase activity are presented in Miller Units and were determined as described in FIG. 2. The results represent the average of four experiments.
In FIG. 3E, concentrations of the selenium-containing derivatives (as indicated) were determined by Atomic absorption Spectrophotometry (AAS) using the varians graphite furnace SpectrAA 300 Zeeman Atomic Spectrophotometer. This Spectrophotometer has an automatic background correcting system; a solution of 0.1% nitric acid and palladium was used as a chemical modifier (10 μl of 500 μg/ml). SeO$_2$ (c[Se]= 1.000±0.002 g/l) was used as a standard selenium solution. For the final estimate for each sample, the mean values for three sequential injections of aliquots were used.
Figure 3B:
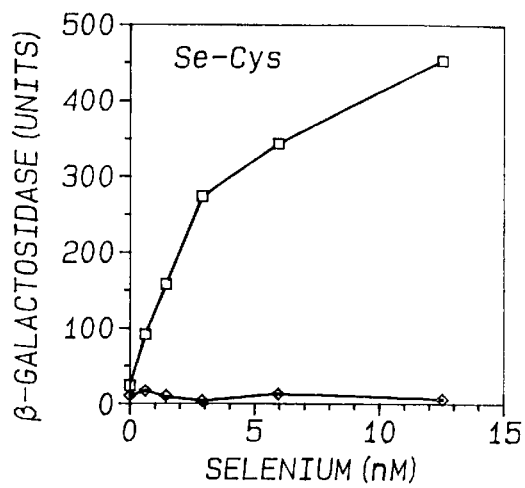

In in vivo experiments, plasmids carrying the inserted fdhF sequences directed selenium incorporation into a fused polypeptide product (FIGS. 1A and 1C) which has β-galactosidase activity that is selenium-dependent (FIG. 2). Since neither the fused protein nor β-galactosidase activity are obtained in selC derivatives lacking the gene for tRNA$^{Sec}$, it is suggested that selenium is incorporated in the form of selenocysteine (FIGS. 1B, 1D and 2). Furthermore, the level of β-galactosidase is proportionally and specifically related to the simple selenium derivatives selenite and selenocysteine (FIGS. 3A and 3B). Thus, the present system of plasmids in appropriate $E.$ $coli$ strains can be used as a bio-assay for determining the selenium concentrations in these compounds. Either plasmid pRM2 or plasmid pRM4 can be used [Reches et al. (1994) Appl. Env. Microbiol. 60:45–50]. However, plasmid pRM4 is preferred since it directs slightly higher levels of the selenium-dependent β-galactosidase activity (FIG. 2). This is probably because, unlike pRM2, pRM4 carries the nine additional nucleotides which precede the 47 nucleotides following the TGA of $E.$ $coli$ gene fdhF (See Table 1B).

The invention therefore relates to plasmids carrying a selenium-specifying DNA sequence of the $E.$ $coli$ fdhF gene upstream of the $E.$ $coli$ lac'Z gene which permits the incorporation of selenocysteine into β-galactosidase.

Specific plasmids according to the invention are those comprising at their beginning a lacZ derivative carrying at least the −9 to +47 nucleotide bases of the TGA codon region of $E.$ $coli$ fdhF gene.

A preferred plasmid according to the invention is a plasmid comprising at its beginning a lac'Z derivative consisting of nucleotide bases −9 to +47 or the TGA codon region of $E.$ $coli$ fdhF gene.

Another preferred plasmid comprises at its beginning a lac'Z derivative consisting of nucleotide bases −1 to +47 of the TGA codon region of $E.$ $coli$ fdhF gene.

Most preferred are plasmids pRM2 deposited at the ATCC under No. 75594 pRM4 deposited at the ATCC under NO. 75595.

In a further aspect, the invention relates to microorganisms transformed with a plasmid according to the invention, having selenium-dependent β-galactosidase activity, $E.$ $coli$ strains being preferred.

Particularly preferred microorganisms are $E.$ $coli$ strains transformed with plasmid pRM2 or with plasmid pRM4.

Additionally, the invention relates to a method for the quantitative determination of selenium in selenium derivatives in a biological samples comprising incubating transformed microorganisms according to the invention in a suitable medium also containing said sample and measuring the level of β-galactosidase activity.

In preferred embodiments, the method according to the invention employs transformed $E.$ $coli$ strains.

The method according to the invention is particularly suitable for the determination of biologically active selenium derivatives, for example sodium selenite or selenocysteine.

By the method according to the invention, selenium derivatives can be quantitatively assayed in different biological materials such as blood, food, and others [Zhao et al. (1994) Gene 148:351–356]. For assaying samples which contain relatively large amounts of protein, particularly blood samples, it is preferably to first subject the sample to acid-vapor treatment, under which proteins undergo hydrolysis.

Thus, in a preferred embodiment for assaying selenium in protein-containing samples, particularly blood samples, the sample is first subjected to acid-vapor treatment, and are then incubated with transformed microorganisms according to the invention in a suitable medium in accordance with the method of the invention, followed by measuring the level of β-galactosidase activity.

In a preferred embodiment HCl vapor is used.

The present invention further provides a bioassay which permits the sensitive determination of selenium concentration on agar plates even more rapidly and easily than does applicants' liquid assay. Similar to the liquid assay, the agar plate version of the assay also permits screening of the selenium status in biological fluid like blood.

More specifically, this method utilizes a fluorescence detector, such as photography, to detect fluorescence from a media, preferably agar, obtained through β-galactosidase activity. Thus, most generally, the assay can be applied and/or adopted to be used as a rapid, efficient and sensitive determination of elements for which the lac'Z gene has been engineered as a reporter gene.

The method preferably utilizes derivatives of 4-methyllumbelliferyl. Sigma Chemical Co., St. Louis, Mo. is capable of making customer derivatives. Examples of such are 4-methylumbelliferyl-β-D-galactoside, 4-methylumbelliferyl-α-D-gluocoside; 4-methyllumbelliferyl-α-D-gluocoside; 4-methyllumbelliferyl β-D-glucuronide; 4-methylumbelliferyl p-guanidinobenzoate; 4-methylumbelliferyl heptanoate; 4-methylumbelliferyl α-L-iduronide; 4-methylumbelliferyl β-D-lactoside. This list is not exhaustive. Preferably for the present invention, 4-methylubelliferyl-β-D-galactosidase is used.

A diagnostic kit for the quantitative determination of selenium derivatives, employing the transformed microorganisms and methods of the invention is also within the scope of the application.

The assays currently available for determining selenium concentrations in various compounds are mainly physical or chemical methods by which the element selenium is determined directly [Ihnat et al. (1986) ibid.; Neve (1991) ibid.].

Figure 3C:
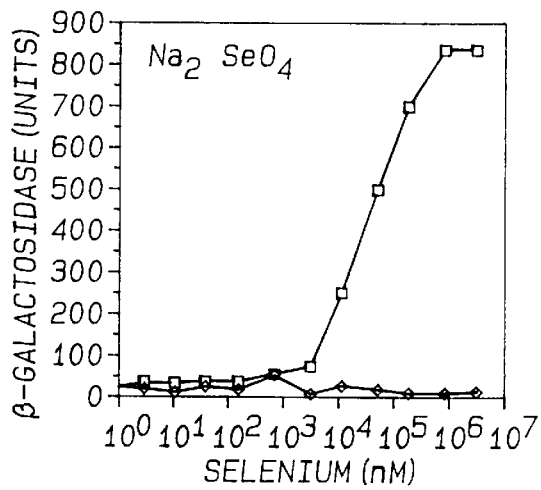
Figure 3D:
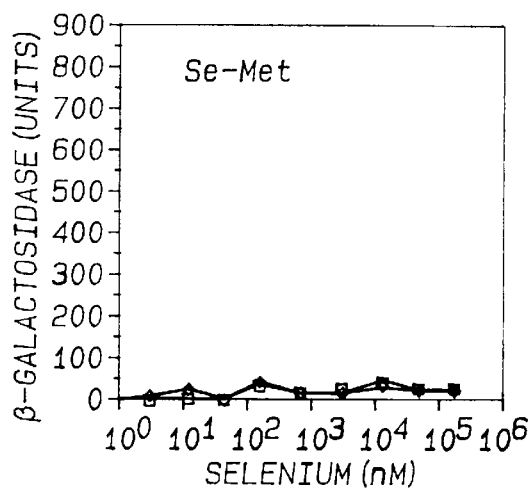
Figure 3E:
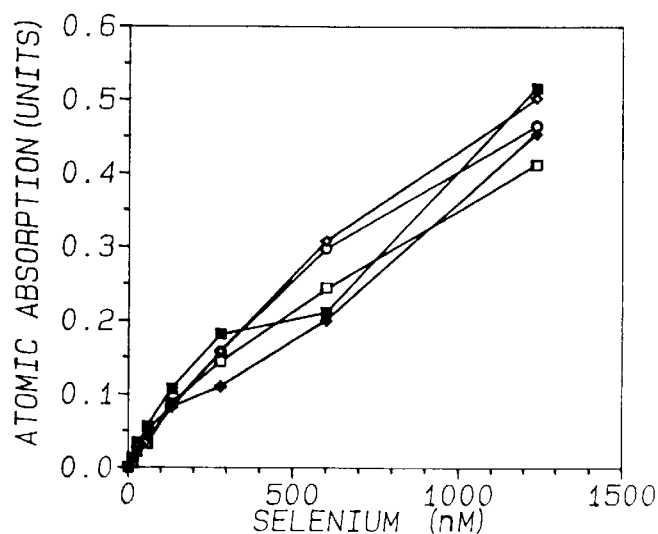

Since one of the best method for this purpose is direct Atomic Absorption Spectrophotometry, the atomic absorption of selenium in various simple selenium derivatives including sodium selenite, sodium selenate, selenocysteine, and selenomethionine, using selenium dioxide solutions as a standard (FIG. 3E) was measured. As is shown in the following examples, the atomic absorption method can be used to measure the selenium concentrations in each of these compounds, and in the range of 2–100 ng Se/ml the results are linear and are similar for all the compounds. In comparison to this physical method, the bioassay according to the invention, which reflects UGA directed selenium incorporation, is more specific because it responds to only a few simple selenium derivatives. Probably because sodium selenite FIG. 3A) and selenocysteine (FIG. 3B) can penetrate the cells and are included in the biochemical pathway of *E. coli* UGA-directed selenocysteine incorporation, the levels of β-galactosidase activity are a linear function of low concentrations of these compounds. On the other hand, because of these same criteria, the bioassay cannot be used to measure selenium in either sodium selenate (FIG. 3C) or selenomethionine (FIG. 3D). In addition, the bioassay is sensitive to sodium selenite and selenocysteine at concentrations (0.07–1.0 ng Se/ml) (FIG. 3A) about 40 times lower than those can be measured by Atomic Absorption Spectrophotometry (2–100 ng Se/ml) (FIG. 3E).

As described herein, the bioassay of the invention is suitable for determining selenium concentrations either in the inorganic form selenite or in the simple organic form slenocysteine. Bacteria cannot use selenium when it is in complicated organic forms. For example, in order to use the bioassay to measure the selenium in proteins like GPX, 5' deiodinase or selenoprotein P, the protein must first be converted to a simple inorganic or organic form by proteolysis. Thus, the basic method of the invention may be modified such that samples are first subjected to acid-vapor treatment, conditions known to the cause hydrolysis in proteins. FIG. 4 shows the effects of acid treatment of various Se-containing compounds on their ability to stimulate the expression of the Se-reporter system. The levels of β-Gal were found to be linearly proportional to the concentrations of sodium selenite, sodium selenate, or selenocysteine in the sample solutions.

The bioassay according to the invention has several advantages over currently available physical assays. The physical assays require sophisticated instruments not always available in clinical laboratories. The present recombinant DNA bioassay, preferably carried out in *E. coli.*, is simple and relatively inexpensive. In addition, at least for sodium selenite and selenocysteine, the present bioassay is sensitive at lower concentrations than is Atomic Absorption Spectrophotometry (FIG. 3E), one of the best available physical methods. A major advantage of the bioassay of the invention is that, unlike the physical methods, it is specific only for certain simple selenium derivatives like selenite or selenocysteine.

Measuring the total selenium status of a biological sample (like blood) can be misleading. For example, the physical methods available (FIG. 3E) are also sensitive to a selenium when it is in the form of a selenomethionine which is incorporated into proteins as a random substitute for methionine [Cowie, D. B. et al., (1957) Biochem. Biophys. Acta 26:252–261; Sliwkowski, M. X. and Stadtman, T. C. (1985) J. Biol. Chem. 260:3140–3144; Frank et al., (1985) J. Biol. chem. 260:5518–5528; Beilstein, et al., (1986) J. Inorg. Biochem. 33:31–46], unlike selenocysteine which, directed by a UGA-codon, is incorporated into the active sites of specific selenoproteins like GPX. Thus, in relation to human health, using a bioassay limited to measuring biologically active forms of selenium is preferable than using unrestricted physical methods. Therefore, the new selenium bioassay of the invention, restricted to reflecting the UGA directed incorporation of selenocysteine, appears to be a better indicator for studies on the relation of selenium and human health than other assays currently available, since it measures specific selenium compounds included in the pathways of "real" selenoproteins.

Figure 5A:
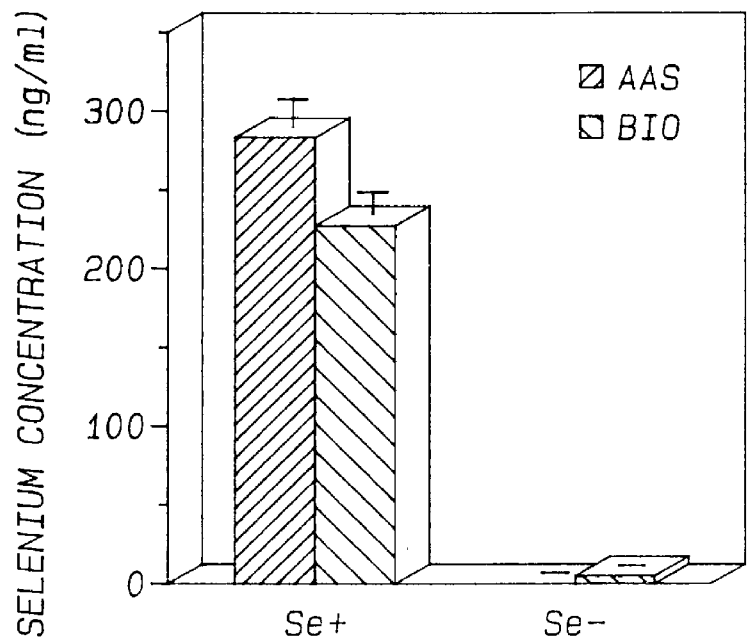
FIG. 5 Se status in blood serum. Selenium status in blood serum samples of rats fed [Se(+)] or [Se(−)] diets was determined by the present bio-assay, AAS and GPX activity. A: Determination by the bio-assay as described in FIG. 3. 50–100 μl blood serum samples were subjected to HCl-vapor hydrolysis prior to assay. Before determining Se levels by AAS, the blood serum samples were diluted ¹/₄₀ to prevent viscosity. B: GPX activity was quantitated by the coupled enzyme procedure of Lawrence and Burk [Biochem. Biophys. Res. Comm. (1976) 71, 952–958]. The results of the measurements by the bio-assay, AAS and GPX each represent the average of three independent experiments.
Figure 5B:
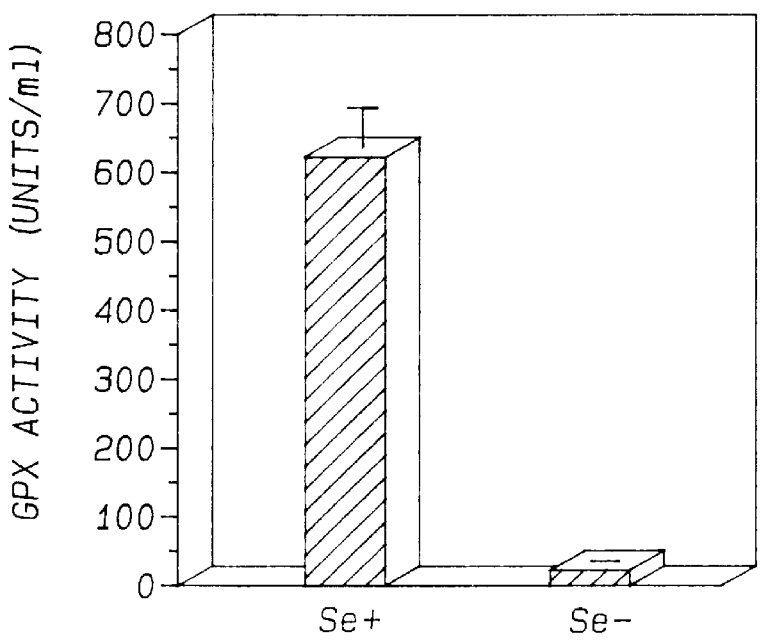

The modified bioassay was tested by using it to determine the Se status in samples of rat blood serum. The results of the bioassay were compared with measurements by two well established methods, Atomic Absorption Spectrophotometry and the level of the activity of the Se-containing enzyme glutathione peroxidase (GPX). Blood serum samples from two groups of rats: (i) Rats fed their usual dies [Se(+)] and (ii) Rats fed a Se-deficient diet [Se(−)] for a six week period was used. The bioassay was used to determine the Se status after the serum samples were subjected to acid hydrolysis (FIG. 5). As shown in FIG. 5A, in the [Se(+)] group, the levels of Se in the sera were 290 ng/ml according to AAS and 240 ng/ml according to the Se bioassay. The level of Se in the sera of the [Se(−)] group was so drastically reduced that it could not even be detected by AAS. However, the bioassay of the invention was sensitive enough to detect Se at the low level of 4 ng/ml, barely 2% of the amount of Se in the sera of the [Se(+)] group. Measured by GPX activity (FIG. 5B), 640 units were found in the sera of the [Se(+)] group and 23 units, or 3,6%, in the sera [Se(−)] group. Thus, the relative amounts of Se found in the sera of the two experimental groups were comparable when measured by the bioassay as a reflection of GPX activity.

The growing implications of selenium in nutrition and medicine support the need for an adequate means of assessing the selenium concentrations in biological materials [Neve (1991) ibid.]. The present recombinant DNA bioassay is both an alternative and an addition to the physical methods currently available.

The invention will be described in more detail in the following examples.

EXAMPLES

SERIES I

Materials and Methods

Materials

[$^{35}$S]-methionine (>800 Ci/mmole) and the sodium salt [$^{75}$Se]-selenite (350 mCi/mmole) (1 Ci=37 GBg) were obtained from Amersham (England). Monoclonal antibodies to β-galactosidase were purchased from Promega (USA). Sodium selenite, sodium selenate, selenomethionine, and selenocystine were obtained from Sigma (USA). Selenocystine was converted to selenocysteine by the addition of approximately 50 times more dithiothreitol (DDT) (Sigma, USA) and incubation at 37° C. for two hours; selenocysteine generation was confirmed by HPLC. Selenium dioxide (SeO$_2$) in HNO$_3$, 0.5 mol/l was obtained from Merck (Germany). Paladium atomic absorption standard solution was obtained from Sigma (USA).

Media

Bacteria were grown in LB or in M9 minimal medium [Miller (1972) ibid.] (pH 7.0) supplemented with 10 µM Na$_2$MoO$_4$ and a mixture of amino acids each at a final concentration of 20 µg/ml. The final concentration of cysteine was 200 µg/ml. Unless otherwise stated, methionine was missing from the media. All the reagents added to M9 medium were analytically pure, and the media were prepared in water double distilled in a Corning water purification system. Ampicillin (100 µg/ml) was add to media in which the plasmid carrying strains were grown.

Bacterial strains and plasmid derivatives.

The E. coli strains and the plasmids used in this study are listed in Table 1A.

TABLE 1-A

E. coli Strains

| Strains/ plasmids | Relevant genotype and characteristics | Source and Comments |
|---|---|---|
| MC41000 | Δ(argF-lac)rpsL150 | CGSC |
| WL81460 | Derivative of MC4100 Δ(srl-racA)306::Tn10 Δ(selC400::Kan | |
| RM1 | Derivative of MC4100 Δ(selC)400::Kan | P1 transduction of Δ(selC)400::Kan from strain WL81460 |
| YN3230 | Derivative of MC4100 Tet$^R$prfB1 | |
| RM2 | Derivative of YN3230 Δ(selC)400::Kan | P1 transduction of (selC)400::Kan from strain WL81460 |

Zinoni et al. (1990) ibid.
Casabadan, M. J. & Cohen S. N. (1979) Proc. Natl. Acad. Sci. USA 76, 4530–4533.
Kopelowitz, J. et al. (1992) J. Mol. Biol. 225, 261–269.
Kawakami et al. (1988) ibid.
E. coli Genetic Stock Center, Yale University

TABLE 1-B

Plasmids

| pMR1 | A pBR322 derivative carrying the fused genes λcI'-lac'I"Z | |
| pMR1(TGAC) | A pMRI derivative carrying a TGA codon followed by a C residue at the junction of AcI'-lac'I"Z. | (24 - supra) |
| pRM2 | A pMR1 derivative carrying the TGA codon region of E. coli gene fdhF (nucleotides −1 to +47) at the λcI-lac'I"Z junction, at the beginning of the lacZ gene. | |
| pRM4 | Like pRM2 except that the TGA region of the E. coli fdhF gene includes nucleotides −9 to +47 | |
| pFM | A pACYC184 derivative carrying the E. coli fdhF gene. | |

Gray, M. A. et al. Proc. Natl. Acad. Sci. USA 79, 6598–6602.
Zinoni et al. (1986) ibid.

Plasmid pFM20 carries the E. coli fdhF [Zinoni et al. (1986) ibid.]. Using the required primers and with plasmid pFM20 as a template, PCR technique was used to amplify two overlapping regions of the fdhF gene flanked by restriction sites HindIII and BamHI: i) the DNA from nucleotides −1 to +47 (plasmid pRM2 ); and ii) the DNA from nucleotides −9 to +47 (plasmid pRM4 ). The nucleotides are numbered relative to the TGA codon of gene fdhF and the positions are indicated by arrows in FIG. 1E.

Molecular cloning.

All of the recombinant DNA manipulations were carried out by standard procedures [Sambrook, J. et al. (1989) Molecular Cloning: A Laboratory Manual (Cold Spring Harbor Lab., Cold Spring Harbor, N.Y.]. Restriction enzymes and other enzymes used in the recombinant DNA experiments were obtained from New England Biolabs (USA). DNA sequencing was carried out using the sequence kit of United States Biochemicals (USA).

Bacterial growth and transformations, and measurements of β-galactosidase activity.

E. coli cells were transformed [Sambrook (1989) ibid.] by the plasmid of choice (see Table 1B). Single colonies of freshly transformed cells were grown on LB plates for six to eight hours and then overnight in M9 medium. On the following day, they were diluted in M9 medium to which a selenium containing derivative was added; the cells were then grown at 37° C. for two to three hours to mid-log phase (OD$_{600}$=0.4–0.6). The cells were examined for β-galactosidase activity in culture aliquots treated with SDS as described by Miller [Miller (1972) ibid.].

Labeling and identification of the in vivo synthesis of the fused gene product λcI'-lac'I"Z.

Freshly transformed cells were grown in M9 medium at 37° C. overnight in the presence of either 1.0 Ci/ml [$^{75}$Se] -selenite or 15 µcI/mi [$^{35}$S]-methionine. During labeling with [$^{75}$Se]-selenite, cold sodium selenite was added to a final concentration of 1.5 µM. Cells were lysed and proteins were extracted and then immunoprecipitated with antibodies to β-galactosidase as described previously [Schoulaker-Schwartz et al. (1991) Proc. Natl. Acad. Sci. USA 88:4996–4500]. Cell lysis and protein extraction were carried out in the presence of 0.2 mM PMSF. Proteins were separated on 7.5% polyacrylamide gels by electrophoresis and detected by autoradiography.

HCl-vapor treatment.

Samples to be treated with HCl vapor were transferred to a 6×50 mm Pyrex tube, dried by vacuum, and sealed into a large vessel to which 6N HCl had been added at the bottom. This procedure permits the acid vapor only to be in contact with the sample. Vapor-phase was carried out under vacuum at 110° C. for 48 hours. The dried samples were suspended in M9 minimal medium and added to the bacterial culture.

Preparation of sera.

Weanling Sprague-Dawley rats (40–50 g) were obtained from Charles River Laboratories (Wilmington, Mass.). For each experimental procedure, two groups of four rats each were fed a torula yeast-based, semi-synthetic [Se(+)] or [Se(−)] diet (Teklad Premier, Madison, Wis.). The Se deficient [Se(−)] diet (product #TD86298) contained 0.016 mg Se/kg; the Se replete [Se(+)] control diet (product #TD87177) had the same formulation but was supplemented with 0.1 mg Se/kg in the form of sodium selenite (Na$_2$SeO$_3$). After six weeks, sera were prepared from blood samples taken from all four rats of each group. Care of the rats and all experimental protocols were done in accordance with the appropriate institutional guidelines and the approval of the Animal Review Committee of Dartmouth Medical School, Lebanon, N.H.

GPX activity.

GPX activity was quantitated by the coupled enzyme procedure of Lawrence and Burk [ibid.]. The reaction mixture contained 50 mM potassium phosphate buffer (pH7) 1 mM EDTA/1 mM Na$n_3$/1 mM GSH/ and 1 E.U./ml glutathione reductase per ml. The serum sample (0.1 ml) was added to 0.8 ml of reaction mixture and pre-incubated for five minutes at 25° C. before the reaction was initiated by the addition of 0.1 ml $H_2O_2$ (2.5 mM). Absorbance at 340 nm was recorded for five minutes. One unit of activity catalyzes the oxidation of 1.0 μmol of NADH reduced per minute. In order to correct for background, distilled water was used instead of the sample.

RESULTS

A reporter system for detecting UGA-directed selenocysteine incorporation into a polypeptide.

Recombinant DNA technology had been previously used by the present inventors to construct a reporter system for sensitively detecting UGA readthrough by tryptophanyl-tRNA$^{Trp}$ in E. coli [Kopelowitz (1992) ibid.]. The present system has been constructed for detecting UGA readthrough by selenocysteinyl-tRNA$^{Sec}$. For this purpose plasmid pMR1 which carries the fused genes λcI'-lac'I"Z {Kopelowitz (1992) ibid.; Gray (1982) ibid.] was used. At the junction of these genes, regions surrounding the TGA codon of the E. coli fdhF gene were inserted; these sequences have been found to permit selecocystein incorporation into polypeptides [Zinoni (1990) ibid.]. The plasmid carrying the region of fdhF from −1 to +47 is called pRM2, and that carrying region −9 to +47 is called pRM4 (and see Materials and Methods and FIG. 1E).

In the E. coli MC4100 derivatives examined, the fused genes λcI'-lac'I"Z of pMR1 direct the synthesis of a 140kD polypeptide. This polypeptide is labeled by [$^{35}$S]-methionine (slot 1 of FIG. 1A and 1B), but not by [$^{75}$Se]-selenite (slot 1 of FIGS. 1C and 1D). On the other hand, in strain MC4100, the protein product of the gene fusions on plasmids pRM2 and pRM4 is labeled by [$^{75}$Se]-selenite (FIG. 1C, slots 2 and 3). As expected, there was no radioactive label incorporated in strain RM1, a selC derivative of MC4100 (slots 2 and 3 of FIGS. 1B and 1D). Thus, the radioactivity in the product of the fused genes of pRM2 and pRM4 is in the form of selenocysteine.

Release factor 2 (RF2) competes with natural or mutated UGA suppressors for the recognition of the UGA codon [Caskey, (1980) TIBS. 5:234–237; Curran et al (1986) Proc. Natl. Acad. Sci. USA 83:6538–6542]; mutation prfB1 is the gene specifying for RF2 increased UGA suppression by a UGA suppressor tRNA and UGA readthrough by tRNA$^{Trp}$ [Kopelowitz (1992) ibid.; Kawakami, et al. (1988) J. Bactriol. 170:5378–5381; Roesser et al. (1989) J. Biol. Chem. 264:12284–12288]. To check whether the prfB1 mutation increase the level of UGA-directed selenocysteine incorporation, a derivative of E. coli strain MC4100, called YN3230, that carries a prfB1 mutation [Kawakami (1988) ibid.] was included in the experiment. By labeling with [$^{75}$Se]-selenite or [$^{35}$Se]-selenite or [$^{35}$Se]-methionine it was found that this mutation had no effect on the UGA-directed selenocysteine incorporation into the λcI'-lac'I"Z product of either pRM2 or pRM4 (data not shown). However, quantitative measurements of β-galactosidase activity levels revealed that the prfB1 mutation did slightly affect the selenium-dependent synthesis of the protein fusion products of both plasmids pRM2 and pRM4 (FIG. 2). As shown in FIG. 2, the level of the synthesis of β-galactosidase is selenium independent when directed by pMR1, which has no TGA codon at the cI-lac'I"Z junction. In strain MC4100 the levels of β-galactosidase directed by pRM2 was 22% and by pRM4 was 24% (FIG. 2A); in strain YN3230 that was directed by pRM2 was 25% and that by pRM4 was 31% (FIG. 2B). These values include 2% selenium-independent β-galactosidase synthesis which is directed by either pRM2 or pRM4 in strains MC4100 and YN3230 in the absence of selenium or in the selC derivatives of these strains in the presence of selenium (FIG. 2). Experimental work was continued with plasmid pRM4 in strain YN3230 where the highest levels of selenium-dependent β-galactosidase activity was found.

The bioassay for determining the presence and concentration of selenium in various simple selenium derivatives. Finally, the selenium-dependent β-galactosidase activity directed by the gene fusion λcI'-lac'I"Z of pRM4 in YN3230 was examined as to whether it could be used as a measure for determining the concentrations of simple selenium derivatives in solutions. As shown in FIG. 3, the levels of β-galactosidase are linearly related to the concentrations of both sodium selenite and slenocysteine. For sodium selenite, linearity is in the range of 0.06–1.0 ng Se/ml (FIG. 3A) for selenocysteine in the range of 2–30 ngSe/ml (FIG. 3B). However, for sodium selenate and selenomethionine this is not the case. Levels of β-galactosidase activity are a function of the logarithm of the concentration of sodium selenate only at very high concentrations of $10^3$–$10^5$ ngSe/ml) (FIG. 3C); no β-galactosidase activity at all was found in the presence of selenomethionine with (data not shown) or without added methionine (FIG. 3D).

For comparison, the concentrations of selenium using each of the described derivatives by the well known Atomic Absorption Spectrophotometric procedure was also determined. As shown (FIG. 3E), for each of the derivatives studied, in the range of 2–100 ng Se/ml absorption was a linear function of the concentration of selenium in the compound.

Acid treatment.

Bacteria cannot use Se when it is incorporated in complicated organic forms, as it is in blood proteins. To overcome this limitation, the above-described bioassay of the invention may be modified so that samples are first subjected to acid-vapor treatment, conditions known to cause hydrolysis in proteins.

FIG. 4 shows the effects of acid treatment of various Se-containing compounds on their ability to stimulate the expression of the Se-reporter system. The levels of β-Gal are found to be linearly proportional to the concentrations of sodium selenite, sodium selenate, or selenocysteine in the sample solutions. As already mentioned, the response of the basic bioassay to these compounds is also dependent on the presence of the E. coli SelC gene (FIG. 4A–4C) which specifies for tRNA$^{Sec}$ [Leinfelder et al., (1988) Nature:331, 723–725]. Furthermore, for each of these three Se derivatives, the linearity of the response is in the range of 0.05–1.0 ng Se/ml (FIGS. 4A–4C). These values are about 20 times lower than the range of sensitivity of the method of AAS (FIG. 4E). In addition, in the case of sodium selenate the linearity of the β-Gal activity is in the range of 0.05–1.0 ng Se/ml, but only after the samples are subjected to acid conditions. This is probably because selenate, which presumably neither penetrates E. coli cells nor is utilized by them, is converted under the acidic conditions to selenite, which does penetrate the cells and is included in the UGA-directed selenocysteine pathway. It may be noted that without the acid-vapor step, the bioassay is not at all sensitive to selenomethionine, which is not included in the UGA directed selenocysteine pathway, even after acid hydrolysis treatment (FIG. 4D).

Blood serum assay.

The modified bioassay was tested by using it to determine the Se status in samples of rat blood serum. The results of the bioassay were compared with measurements by two well established methods, AAS (see above) and the level of the activity of the Se-containing enzyme GPX. Blood serum samples from two groups of rats was used: (i) Rats fed their usual diet [Se(+)] and (ii) Rats fed a Se-deficient diet [Se(−)] for a six week period. The bioassay was used to determine the Se status after the serum samples were subjected to acid hydrolysis (FIG. 5). As shown in FIG. 5 A, in the [Se(+)] group, the levels of Se in the sera were 290 ng/ml according to AAS and 240 ng/ml according to the selenium bioassay. The level of Se in the sera of the [Se(−)] group was so drastically reduced that it could not even be detected by AAS. However, the bioassay of the invention was sensitive enough to detect Se at the low level of 4 ng/ml, barely 2% of the amount of Se in the sera of the [Se(+)] group. Measured by GPX activity (FIG. 5B), 640 units in the sera of the [Se(+)] group and 23 units or 3,6%, were found in the sera [Se(−)] group. Thus, the relative amounts of Se found in the sera of the two experimental groups were comparable when measured by the present bioassay or as a reflection of GPX activity.

EXAMPLES

SERIES II

Materials and Methods

Materials 4-methylumbelliferyl-β-D-galactoside (MUG), sodium selenite, selenomethionine, and selenocystine were obtained from Sigma Chemical Co. (St. Louis, Mo., USA). Selenocystine was converted to selenocysteine by the addition of approximately 50 times more dithiothreitol (Sigma) and incubation of 37° C. for two hours. Agar Nobel was obtained from Difco Laboratories (Detroit, Mich., USA).

Media and solutions.

Bacteria were grown in YT or in M9 minimal medium [Miller et al. (1972) Experiments in Molecular Genetics, p. 351–356. Cold Spring Harbor Laboratory Press, Cold Spring Harbor, N.Y.] (pH 7.0) supplemented with 0.4% glucose and arginine at a final concentration of 20 mg/mi. Soft top agar contained 0.8% Agar Noble and 0.8% NaC1. Bottom Agar contained 1.8% Agar Noble in M9 medium. All the reagents added to M9 medium were analytically extra-pure and the medium was prepared in water distilled by passing through columns of Nanopure purification system from Barnstead Co. (Dubuqe, Iowa, USA). Ampicillin (100 μg/ml was added to media in which the plasmid-carrying strain was grown. MUG was suspended at concentrations of 0.1% in dimethyl sulfoxide (DMSO).

Bacterial strains and plasmids.

The E. coli strains used were YN3230 Δ(argF-lac) rpsL150 prfB1 tet$^r$ [Kawakami et al., (1988) J. Bacteriol. 170:5378–5381; Kopelowitz et al (1992) J. Mol. Biol. 225:261–269] and RM2, a ΔselC derivative of YN3230 [Reches et al. (1994) J. Appl. Env. Microbiol. 60:45–50]. n Plasmid pRM4 is a pBR322 derivative carrying fused genes λcI'lacI"Z [Kopelowitz et al. (1992) ibid.] in which the TGA codon region of the E. coli fdhF gene (nucleotides −7 to +47) was inserted in the junction of the λcI'-lacI"Z gene fusion. All the plasmids carry ampicillin resistance.

Determination of selenium concentration on agar plates using the β-galactosidase-MUG fluorescence assay.

E. coli strains YN3230 or RM2 were transformed with plasmid pRM4 as described above. A colony of newly transformed cells was grown overnight on YT agar plates containing 100 μg/ml ampicillin; the cells were then suspended in 2 ml M9 liquid medium with ampicillin and grown on a rolling drum at 37° C. for seven hours (OD600 1.0+0.2). 50 μl of this culture were mixed with 2 ml of soft top agar and poured over the surface of M9 bottom agar plates containing different concentrations of various compounds to be tested for selenium. The plates were incubated at 37° C. overnight. The next day 1 μl of 0.1% MUG solution was placed on the surface of each plate, and incubated at 37° C. for ten minutes. The plates were UV irradiated at 312 nm and photographed by Strategene Eagleeye II computerized video camera or by a simple Polaroid camera. Determination of selenium concentration in rat blood serum samples using the β-galactosidase-MUG-fluorescence assay on agar plates.

Rat blood sera was received from Drs. D. Depalo and D. L. St. Germain of Dartmouth Medical School (Lebanon N.H., USA) [Zaho et al. (1994) ibid.]. They used weanling Sprague-Dawley rats (40–50 g) obtained fro the Charles River Laboratories (Wilmington, Mass., USA). These rats were normally fed on a torula yeast-based semi-synthetic diet. Six weeks before their blood was drawn for selenium concentration testing, half the rats were randomly chosen to remain on their regular diet —Se(+)] (A) and the other half were fed a selenium-deficient diet [Se(−)](B).

The rat blood serum samples were subjected to HCl-vapor hydrolysis as described above [Zhao et al. (1994) ibid.]. As a control, the selenium concentrations in the serum samples were determined using both liquid assay by the level of β-galactosidase activity reflected by ONPG-hydrolysis [Reches et al. (1994) ibid.], as well as by the β-galactosidase-MUG-fluorescence agar plate assay of the present invention. In each case the β-galactosidase activity was directed by the presence of pRM4 in strain YN3230 as described previously [Reches et al. (1994) ibid.; Zaho et al (1994) ibid.]. Each of the samples were diluted to within the range detectable by the agar plate assay. It should be noted that the requirement of subjecting the serum samples to HCl-vapor hydrolysis limits the possibility of diluting the samples less than 100 fold.

RESULTS

A bioassay for selenium determination on agar plates based on fluorescence of β-galactosidase cleaved MUG.

In this study the constructed plasmid pRM4 was used that carries a gene-fusion in which is inserted an in-frame TGA codon that specifies for the incorporation of selenocysteine during translation [Reches et al. (1994) ibid.]. This gene-fusion provides a reporter system for determining selenium concentrations when the plasmid containing this reporter construct is present in E. Coli strain YN3230. Applicants previously have shown that the level of β-galactosidase activity in liquid medium is proportionally related to the concentration of several simple selenium derivative like sodium selenite and selenocysteine [Reches et al. (1994) ibid.]. Here, the level of β-galactosidase activity is determined on agar plates. This is done by the use of 4-methylumbelliferyl-β-D-galactoside (MUG): when MUG is cleaved by β-galacotosidase, the released 4-methylumbelliferyl moiety fluoresces [Robinson et al. (1967) Biochem. J. 102:525–532].

In the experiments described here, E. coli YN3230 cells newly transformed by pRM4 were plated on M9 agar plates containing different concentrations of selenium compounds. In particular, blood serum containing different selenium concentrations was used. After overnight growth, drop of MUG was added to bacterial lawns on each plate, and fluorescence was detected by UV irradiation and photographed by either a Polaroid camera or a video camera.

As shown, with host cells YN3230 and in the sodium selenite concentration range of 0.2–0.8 ng/ml, the intensity of fluorescence in the plates is proportional to the concentration of sodium selenite (FIG. 6B plates 1–3). The intensity of fluorescence was also quantitated by computer analysis. As shown FIG. 6C, a linear curve was obtained that was used as a standard curve for determination of selenium in blood (see below). In addition, similarly to previously described liquid selenium bioassay [Reches et al. (1994) ibid.], also the β-galactosidase-MUG-fluorescence test on agar plates does not respond to selenomethionine (data not shown).

Use of β-galactosidase-MUG-fluorescence assay for the determination of selenium blood.

The selenium bioassay is carried out in bacteria that cannot use selenium when it is incorporated in complicated organic forms, as it is in blood proteins. To overcome this limitation, the original bioassay [Zaho et al., (1994) ibid.] was modified, the blood samples are first subjected to HCl-vapor treatment, conditions known to cause protein hydrolysis.

Rat blood serum samples used were provided by Drs. D. Depalo and D. L. St. Germain (Lebanon N.H. USA) [Zaho et al., (1994) ibid.]. The rats had been kept either (A) on a regular diet [Se(+)] or (B) on a selenium-deficient diet [Se(−)] (see Materials and Methods). The serum samples were subjected to HCl-vapor hydrolysis as described previously Reches et al. (1994); Zaho et al. (1994)]. As a control, the selenium concentrations in the serum samples were determined using both our liquid assay in which β-galactosidase activity was reflected by ONPG-hydrolysis, as well as the present β-galactosidase-MUG-fluorescence agar plate assay. In each case, the β-galactosidase activity was directed by the presence of pRM4 in strain YN3230 as described previously [Reches et al. (1994)].

Each of the samples was diluted to within the range detectable by the agar plate test. Note that the requirement of subjecting the serum samples to HCl vapor hydrolysis limits the ability to dilute the samples less than 100 fold.

As measured by the liquid bioassay, the concentration of selenium was 240 ng/ml in the [Se(+)] samples and 3.3. ng/ml in the [Se(−)] samples. FIG. 7 shows the selenium concentrations in these blood serum samples as detected by the β-galactosidase-MUG-fluorescence assay on agar plates. As shown (FIG. 7A, plates 1–3), according to this method, the level of selenium in the [Se(+)] sample is also about 240 ng/ml. When diluted 1200, 600 and 300 fold the level of fluorescence reflects selenium concentrations of 0.2, 0.4, and 0.8 ng/ml., (±5%) respectively. This was done by computer analysis of the photographed plates, using the selenium standard curve (FIG. 6C) for the quantitative determination. Selenium in the [Se(−)] serum sample was not detected (FIG. 7B plates 1–3). However, as mentioned above, the acid vapor treatment for protein hydrolysis precludes dilutions less than 100 fold. Since the lower limit of selenium detection is 0.2 ng (FIG. 6A, plate 1), the negative results with the {Se(−)] serum sample indicate that the level of selenium was below 20 ng/ml.

Three technical notes are: (i) The new agar plate version of the bioassay described here required the use of analytically extra-pure reagents and water distilled by a very high standard purification system. This is because the agar plate bioassay is so sensitive that even trace amount of selenium found in the water in the reagents lead to false-positive results. (ii) For quasi-quantitative measurements of the selenium status, even a simple Polaroid camera can be used to photograph the intensity of the fluorescence obtained by the cleavage of MUG by β-galactosidase. The use of a computerized video camera permits the measurements of the fluorescence to be specifically quantitated (FIG. 6C). (iii) At the low end of the range of selenium concentrations (0.2 ng/ml) for which the assay is accurate, fluorescence is not well detected photographically; however, the fluorescence can be detected visually.

Discussion

Figure 6:
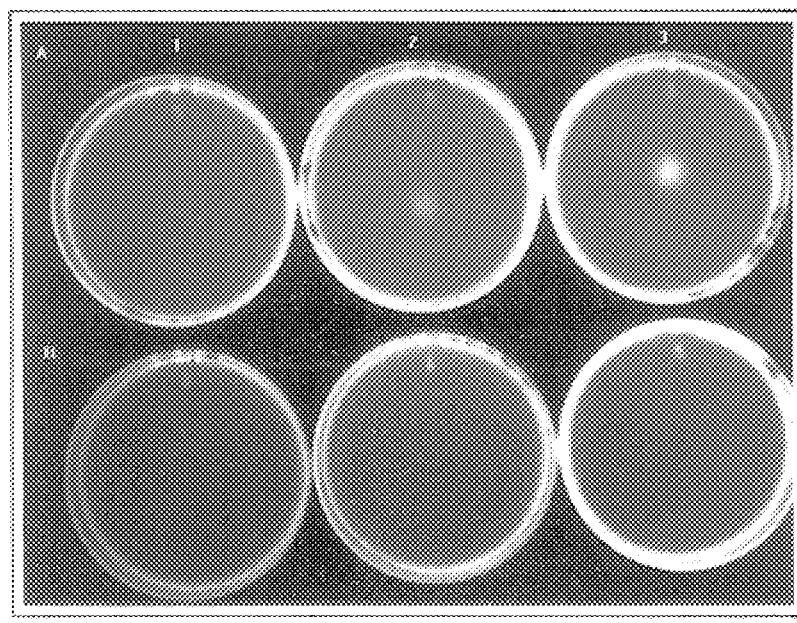
FIG. 6 is a graph showing the use of the β-galactosidase-MUG-fluorescence assay on agar plates to determine the intensity of fluorescence resulting from the presence of various concentrations of sodium selenite. Plasmid pRM4 was used to transform *E. coli* strains YN3230 (A) or its ΔselC derivative RM2 (B). The transformed cells were plated and grown on agar plates containing various concentrations of selenite. The intensity of the fluorescence of the MUG moiety cleaved by β-galactosidase was detected as described in "Materials and Methods". The concentrations of selenite used were: (1) 0.2 ng/ml; (2) 0.4 ng/ml; (3) 0.8 ng/ml. The standard selenium concentration curve (C) was obtained by the quantitation of selenite concentration of (A) versus the intensity of fluorescence using NIH Image 1.41 program for computer analysis. The values represent arbitrary units of the color density measured on a black-white scale.
Figure 7A:
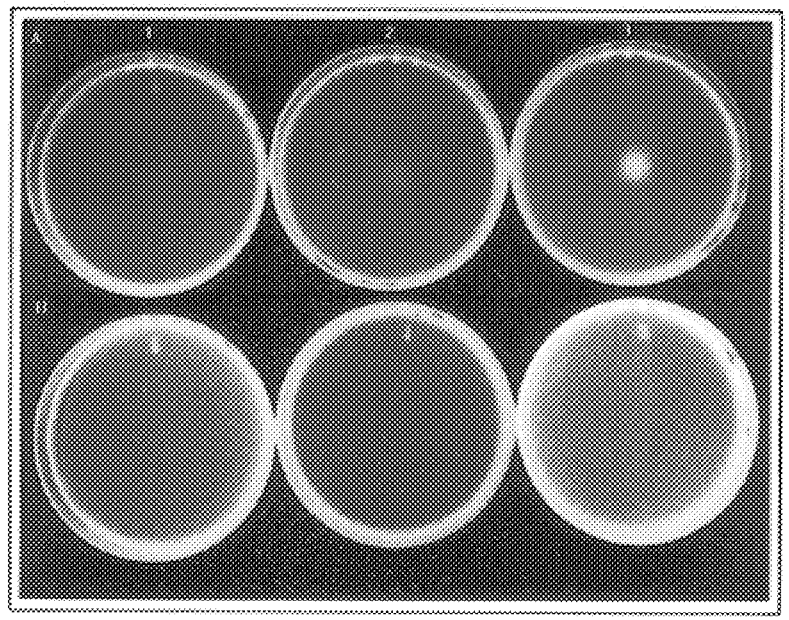
FIG. 7 Use of the β-galactosidase-MUG-fluorescence assay to determine the intensity of fluorescence resulting from testing rat blood serum samples containing high or low selenium concentrations. Rat blood serum samples from rats fed normal fed [Se(+)] (A) or on selenium deficient feed [Se(−)] (B) were subjected to HCl-vapor hydrolysis. As determined by the use of liquid bioassay (described previously, 33) (data not shown), the concentration of selenium in the blood plasma samples from normally fed rats (A) was 240 ng/ml; the concentration of selenium in the blood plasma samples from selenium starved rats was only 3.3 ng/ml. The samples were serially diluted and their respective selenium concentrations were re-tested by β-galactosidase-MUG-fluorescence assay (as described in FIG. 6). The flowing dilutions were tested (the resulting selenium concentrations are shown in parentheses): (A-1)× 1200 (0.2 ng/ml); (A-2)×600 (0.4 ng/ml); (A-3)×300 (0.8 ng/ml); (B-1)×600 (0.005 ng/ml); (B-2)×300 (0.01 ng/ml); (B-3)×100 (0.03 ng/ml).
Figure 7B:
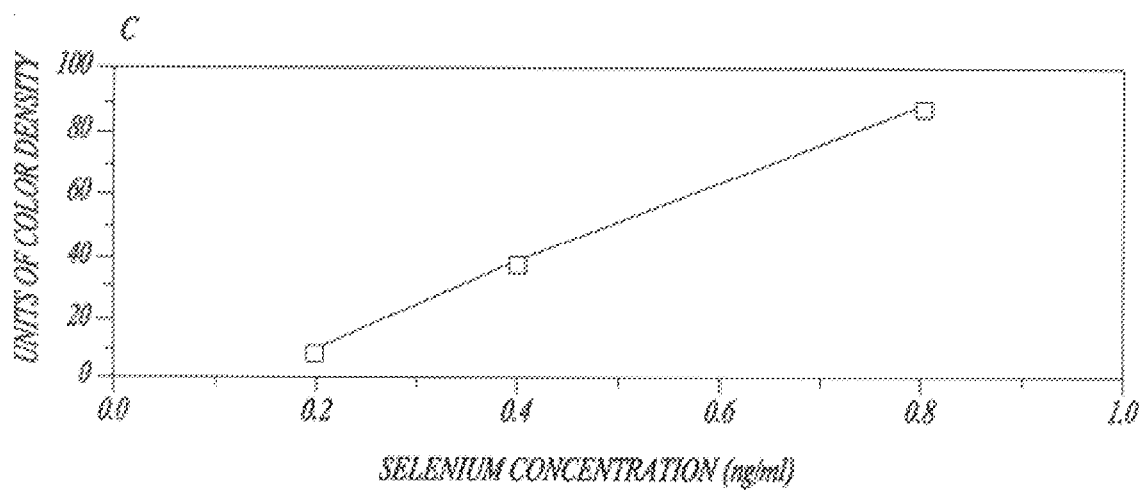

This version of the present inventive recombinant DNA bioassay enables a rapid quantitative determination of selenium concentrations on agar plates sensitive within the range of 0.2–0.8 ng/ml (FIG. 6). This method can also be used to screen the selenium status in blood serum samples (FIG. 7). Moreover, the principle of this method, photography of the fluorescence on agar plates obtained through β-galactosidase activity, can be more generally used for a rapid and sensitive determination of elements for which the lacZ gene has been engineered as a reporter gene.

Selenium, through its involvement in the peroxide destroying enzyme GPX is part of the complex antioxidation mechanism which prevents the accumulation of the free radicals [Michiels et al., (1994) Free Radic. Biol, Med. 17:235–248] and thereby is probably involved in the prevention of apoptosis Hockenberg et al. (1993) Cell 75:241–251] and various free radical diseases like cancer (Halliwell et al. (1989) Free Radicals in Biology and Medicine, 2nd ed. Clarendon Press, Oxford; Neve, et al. (1991) Experiments 47:187–193; Olano, (1990) Neurology 40:32–37; Read (1990) New Scientist 125:38–42]. So far, however, inadequate levels of selenium intake in humans have been clearly shown to be associated with only two diseases, Keshan disease [Yang et al. (1984) The role of Selenium in Keshan disease, p. 203–231, In H. H. Draper (ed.) Advances in Nutritional Research. Plenum Press, New York] and Kachin Beck disease [Jiang et al. (1989) The relativity between some epidemiological characteristics of Kachin-Beck Disease and selenium deficiency, p. 263–269. In A. Wendel (ed.), Selenium in Biology and Medicine. Springer Verlag, Berlin-Hong Kong.] both occurring in China. Keshan disease is an endemic cardiomyopathy disease [Gu (1983) Chin Med. J. 96:251–261]; Coxsackieviruses have been shown to be a major co-factor with selenium deficiency in this disease Su (1979) Chin. Med. J. 59:466–472]. In addition, it has recently been shown that the normally avirulent Coxsackievirus B3 becomes virulent in a selenium-deficient mouse due to mutations in the viral genome [Beck et al. (1995) Nature Med. 1:433–436]. The work is the first to show that a nutritional deficiency can accelerate evolution of a population from benign to virulent in an intact animal. The role of selenium deficiency in viral diseases has been further suggested in a recent theory that links HIV, and therefore AIDS, to the depletion of selenium from the cells [Taylor et al. (1994) J. Med. Chemistry 37:2637–2654]. The growing implications of the role of selenium in human health suggest a need for an adequate means for assessing the selenium status in biological fluids like blood. The present invention offers rapid and sensitive fluorescence bioassay for this purpose.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims the invention may be practiced otherwise than as specifically describe.

REFERENCES

1. Beck, M. A., P. C. Kolbeck, L. H. Nohr, Q. Shi, and V. C. Morris. 1994. Benign human enterovirus becomes virulent in selenium deficienct mice. J. Med. Virol. 43:166–170.

2. Beck, M. A., Q. Shi, V. C. Morris, and O. A. Levander. 1995. Rapid genomic evolution of a non-virulent Coxsackie virus B3 in Selenium-deficient mice results in selection of identical virulent isolates. Nature Med. 1:433–436.
3. Berg, B. L., C. Baron, and V. Stewart 1991. nitrate-inducible formate dehydrogenase in *Escherichia coli* K-12 II. Evidence that a mRNA stem-loop structure is essential for decoding opal (UGA) as selenocysteine. J. Biol. Chem. 266:22386–22391.
4. Berry, M. J., L. Banu, Y. Chen, S. Y. Mandel, D. Kieffer, J. Harney, and P. R. Larsen. 1991. Recognition of UGA as a selenocysteine codon in type I deiodinase requires sequences in the 3' untranslated region. Nature 353:273–276.
5. Berry, M. J., L. Banu, and P. R. Larsen. 1991. Type I iodothyronine deiodinase is a selenocysteine-containing enzyme. Nature 349:438–440.
6. Böck, A., K. Forchhammer, J. Heider, and C. Baron. 1991. Selenoprotein synthesis: An expansion of the genetic code. Trends Biochem. Sci. 16:463–467.
7. Böck, A., K. Forchhammer, J. Heider, W. Leinfelder, G. Sawers, B. Veprek, and F. Zinoni. 1991. Selenocysteine: The 21st amino acid. Mol. Microbiol. 5:515–520.
8. Chambers, I., J. Frampton, P. Goldfarb, N. Affara, W. McBain, and P. R. Harrison. 1986. The structure of the mouse glutathione peroxidase gene: the selenocysteine in the active site is encoded by the "termination" codon TGA. EMBO J. 5:1221–1227.
9. Gu, B. Q. 1983. Pathology of Keshan disease. A comprehensive review. Chin. Med. J. 96:251–261.
10. Halliwell, B., and J. M. C. Gutteridge. 1989. Free Radicals in Biology and Medicine, 2nd ed. Clarendon Press, Oxford.
11. Heider, J., C. Baron, and A. Böck. 1992. Coding from a distance: dissection of the mRNA determinants required for the incorporation of selenocysteine into protein. EMBO J. 11:3759–3766.
12. Hill, K. E., R. S. Lloyd, J. G. Yang, R. Read, and R. F. Burk. 1991. The cDNA for rat selenoprotein P contains 10 TGA codons in the open reading frame. J. Biol. Chem. 266:10050–10053.
13. Hockenberg, D. M., zn Oltvai, X.-M. Yin, C. L. Milliman, and S. J. Korsmeyer. 1993. Bcl-2 functions in an antioxidant pathway to prevent apoptosis.Cell 75:241–251.
14. Jiang, Y.-F., and G.-L. Xu. 1989. The relativity between some epidemiological characteristics of Kachin-Beck Disease and selenium deficiency, p. 263–269. In A. Wendel (ed.), Selenium in Biology and Medicine. Springer Verlag, Berlin - Hong Kong.
15. Kawakami, K., T. Inada, and Y. Nakamura. 1988. Conditionally lethal and recessive UGA-suppressor mutations in the prfB gene encoding peptide chain release factor 2 of *Escherichia coli*. J. Bacteriol. 170:5378–5381.
16. Kopelowitz, J., C. Hampe, R. Goldman, M. Reches, and H. Engelberg-Kulka. 1992. Influence of codon context on UGA suppression and readthrough. J. Mol. Biol. 225:261–269.
17. Lee, B. J., M. Rajagopalan, Y. S. Kim, K. H. You, K. B. Jacobson, and D. Hatfield. 1990. Selenocysteine tRNA$^{sec}$ gene is ubiquitous within the animal kingdom. Mol. Cell Biol. 10:1940–1949.
18. Michiels, C., M. Raes, O. Toussaint, and J. Remade. 1994. Importance of Se-glutathione perioxidase, catalase, and Cu/Zn— SOD for cell survival against oxidative stress (Review). Free Radic. Biol, Med. 17:235–248.
19. Miller, J. H. (ed.) 1972. Experiments in Molecular Genetics, p. 351–356. Cold Spring Harbor Laroratory Press, Cold Spring Harbor, N.Y.
20. Mullenbach, G. T., A. Tabrizi, B. D. Irvine, G. I. Bell, J. A. Tainer, and R. A. Halliwell. 1988. Selenocysteine's mechanism of incorporation and evolution revealed in cDNAs of three glutathione peroxidases. Protein Engineering 2:239–246.
21. Nève, J. 1991. Physiological and nutritional importance of selenium. Experimentia 47:187–193.
22. Olanow, C. W. 1990. Oxidation reaction in Parkinson's disease. Neurology 40: 32–37.
23. Read, C. 1990. Behind the face of malnutrition. New Scientist 125:38–42.
24. Read, R., T. Bellew, J.-G. Yang, K. E. Hill, I. S. Palmer, and R. F. Burk. 1990. Selenium and amino acid composition of selenoprotein P, the major selenoprotein in rat serum. J. Biol. Chem. 265:17899–17905.
25. Reches, M., C. Zhao, and H. Engelberg-Kulka. 1994. A selenium bio-assay based on recombinant DNA technology for determining selenium concentration. J. Appl. Env. Microbiol. 60:45–50.
26. Robinson, R., G. Price, and N. Dance. 1967. Separation and properties of β-glucuronidase from rat kidney. Biochem. J. 102:525–532.
27. Spinney, L. 1995. Poor diets breed deadly viruses. New Scientist 146:16.
28. Stadtman, T. C. 1991. Biosynthesis and function of selenocysteine-containing enzymes. J. Biol. Chem. 266:16257–16260.
29. Su, C. 1979. Preliminart results of viral etiology of Keshan disease. Chin. Med. J. 59:466–472.
30. Taylor, E. W., C. S. Ramannthan, R. K. Jaluri, and R. G. Wadimpalli. 1994. A basis for new approaches to the chemotherapy of AIDS: Novel genes in HIV1 potentially encodes selenoprotins expressed by ribosomal frameshifting and termination suppression. J. Med. Chemistry 37:2637–2654.
31. Yang, G., J. Chen, Z. Wen, and K. Ge. 1984. The role of Selenium in Keshan disease, p. 203–231. In H. H. Draper (ed.), Advances in Nutritional Research. Plenum Press, New York.
32. Zachara, B. A. 1992. Mammalian Selenoproteins. J. Trace Elem. Electrolytes Health Dis. 6:137–151.
33. Zhao, C., M. Reches, D. Depalo, D. L. St Germain, and H. Engelberg-Kulka. 1994. A DNA recombinant bio-assay for selenium in blood. Gene 148:351–356.
34. Zinoni, F., A. Birkman, W. Leinfelder, and A. Böck. 1987. Cotranslational insertion of selenocysteine into formate dehydrogenase from *Escheiichia coli* directed by a UGA codon. Proc. Natl. Acad. Sci. USA 84:3156–3160.

What is claimed is:

1. A plasmid carrying a selenium-specifying DNA sequence of the *Escherichia coli* (*E. coli*) formate dehydrogenase (fdhF) gene of the −9 to +47 nucleotide bases or −1 to +47 nucleotide bases encoding the TGA region upstream of the *E. coli* lac'Z gene which permits the incorporation of selenocysteine into β-galactosidase.

2. A plasmid according to claim 1 comprising at its beginning a lacZ derivative carrying at least the −9 to +47 nucleotide bases of the TGA codon region of *E. coli* fdhF gene.

3. A plasmid according to claim 2 comprising at its beginning a lacZ derivative consisting of nucleotide bases −9 to +47 of the TGA codon region of *E. coli* fdhF gene.

4. A plasmid according to claim 2 comprising at its beginning a lacZ derivative consisting of nucleotide bases −1 to +47 of the TGA codon region of *E. coli* fdhF gene.

5. Plasmid pRM2 deposited at the ATCC under No. 75594.

6. Plasmid pRM4 deposited at the ATCC under No. 75595.

7. Microorganisms transformed with a plasmid according to claim 1 having selenium-dependent β-galactosidase activity.

8. Microorganisms according to claim 7 being *E. coli*.

9. *E. coli* transformed with plasmid pRM2.

10. *E. coli* transformed with plasmid pRM4.

11. A method for the quantitative determination of selenium in selenium derivatives in a biological sample comprising incubating microorganisms according to claim 7 in a suitable medium also containing said sample and measuring the level of β-galactosidase activity.

12. A method according to claim 11 wherein said microorganism is *E. coli* according to claim 9.

13. A method according to claim 11 wherein said microorganism is *E. coli* according to claim 10.

14. A method according to claim 11 which further comprises a preliminary step in which said biological sample is subjected to treatment with acid vapor prior to being added to incubation medium.

15. A method according to claim 14 wherein in said preliminary step said biological sample is vacuum dried prior to being subjected to said acid vapor treatment.

16. A method according to claim 14 wherein said acid is HCl.

17. A method according to claim 11 wherein said selenium derivative is a biologically active selenium derivative.

18. A method according to claim 17 wherein said selenium derivative is a selenite.

19. A method according to claim 17 wherein said selenium derivative is selenocysteine.

20. A method according to claim 14 wherein said sample is blood.

21. A method according to claim 11 wherein said sample is a food sample.

22. A diagnostic kit for the quantitative determination of selenium in selenium derivatives including microorganisms transformed by plasmids as set forth in claim 1.

23. A method as set forth in claim 11 wherein said measuring step is further defined as adding a compound to the media that is cleaved by β-galactosidase and fluoresces and detecting the emitted fluorescence as a measure of selenium derivatives.

24. A method as set forth in claim 23 wherein the compound added is selected from the group consisting of 4-methylumbelliferore derivatives.

25. A method as set forth in claim 23 wherein said measuring step is further defined as photographing the media to detect the emitted fluorescence.

26. A method as set forth in claim 23 wherein said incubating step is further defined as plating the microorganisms on agar containing the sample.

27. A method as set forth in claim 26 wherein said adding step is further defined as adding the compound that fluoresces to bacterial lawns on the agar after said incubation step.

28. A plasmid carrying a selenium-specifying DNA sequence of the *Escherichia coli* (*E. coli*) formate dehydrogenase (fdhF) gene of the −9 to +47 nucleotide bases encoding the TGA region upstream of a *E. coli* lac'Z gene derivative which permits the incorporation of selenocysteine into β-galactosidase.

29. A plasmid carrying a selenium-specifying DNA sequence of the *Escherichia coli* (*E. coli*) formate dehydrogenase (fdhF) gene of the −1 to +47 nucleotide bases encoding the TGA region upstream of a *E. coli* lac'Z gene derivative which permits the incorporation of selenocysteine into β-galactosidase.

* * * * *